(12) United States Patent
Molieri

(10) Patent No.: US 11,233,927 B2
(45) Date of Patent: Jan. 25, 2022

(54) SYSTEM AND METHOD FOR PRIORITIZING THE SYNCHRONIZATION OF A LIGHT SOURCE WITH IMAGE SENSOR

(71) Applicant: KARL STORZ Imaging, Inc., Goleta, CA (US)

(72) Inventor: Eduardo M. Molieri, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 16/920,120

(22) Filed: Jul. 2, 2020

(65) Prior Publication Data
US 2020/0336634 A1 Oct. 22, 2020

Related U.S. Application Data

(63) Continuation of application No. 16/368,514, filed on Mar. 28, 2019, now Pat. No. 10,742,858.

(51) Int. Cl.
*H04N 5/225* (2006.01)
*H04N 5/235* (2006.01)
*H04N 5/232* (2006.01)

(52) U.S. Cl.
CPC ......... *H04N 5/2256* (2013.01); *H04N 5/2353* (2013.01); *H04N 5/2354* (2013.01); *H04N 5/23232* (2013.01)

(58) Field of Classification Search
CPC .......................... H04N 5/2256; H04N 5/2354
USPC .................................................. 348/370, 371
See application file for complete search history.

(56) References Cited

U.S. PATENT DOCUMENTS

| 5,187,572 | A | 2/1993 | Nakamura |
| 5,749,830 | A | 5/1998 | Kaneko |
| 7,179,222 | B2 | 2/2007 | Imaizumi |
| 9,172,886 | B2 | 10/2015 | Nambakam |
| 9,375,134 | B2 | 6/2016 | Nambakam |
| 9,459,415 | B2 | 10/2016 | Feingold |

(Continued)

FOREIGN PATENT DOCUMENTS

JP 6234212 B2 6/2015

OTHER PUBLICATIONS

Hemb, Björn; Extended European Search Report, dated Jul. 30, 2020, pp. 1-6, Munich Germany, Application No. 20161269.4-1122.

*Primary Examiner* — Anthony J Daniels
(74) *Attorney, Agent, or Firm* — Michael Loi; Honigman LLP

(57) ABSTRACT

A system and method includes operations and steps for synchronizing a light source with an image sensor. An imaging system includes a camera unit having an image sensor, a light detector unit and a synchronization unit. The light detector unit detects the actual time the light source is actuated to determine when a switch occurs between white light and colored light. A camera controller unit processes the actual time with a timing of the image sensor to detect a difference between the actual time the light source is switched and the timing of the image sensor. The camera controller unit is configured to actuate synchronization unit to synchronize the light source with the image sensor when the switch occurs outside of a predetermined period within a blanking region during frame formation.

17 Claims, 9 Drawing Sheets

(56) References Cited

U.S. PATENT DOCUMENTS

2007/0088193 A1  4/2007  Omori
2018/0213141 A1* 7/2018  Pandit .................. H04N 5/2354

* cited by examiner

SYSTEM AND METHOD FOR PRIORITIZING THE SYNCHRONIZATION OF A LIGHT SOURCE WITH IMAGE SENSOR

CROSS-REFERENCE TO RELATED APPLICATIONS

This application is a continuation of U.S. patent application Ser. No. 16/368,514 filed Mar. 28, 2019, the contents of which are incorporated herein by reference.

TECHNICAL FIELD

This disclosure relates to a system and method for the synchronization of light source switching.

BACKGROUND

Endoscopes are commonly used in the medical field for providing access to body cavities with decreased invasiveness. Rigid endoscopes include a rigid insertion tube, while flexible endoscopes typically include a flexible insertion tube. The insertion tubes, which extend from a hand piece or control portion, are configured to be inserted into a body cavity. A distal tip of the insertion tube includes an array of peripherals for providing various functions. For example, the distal tip may include lighting for illuminating the body cavity, one or more ports for delivering air or irrigation, suction ports for removing debris from the body cavity, a medical device or tool, and optics for providing a view of the body cavity to an operator of the endoscope.

Endoscopic systems may include one or more image sensors to provide the surgeon with a video image of the procedure. In some instances, the image sensor may be configured to process electromagnetic radiation in the visible spectrum as well as the infrared spectrum to provide a white light video and/or a fluoroscopic video. In such systems, complementary metal oxide semiconductor (CMOS) sensors are commonly employed in endoscopes due to their ability to provide reduced readout times and faster frame rates. For instance, CMOS may capture up to 60 frames per second.

The image sensor includes a plurality of pixels arranged in a matrix having X number of rows and Y number of columns. The image sensor scans the electromagnetic radiation collected in each row successively to produce an image frame. Upon reaching the last row, the image sensor scans the first row to begin the process of producing another image frame. The speed at which the image sensor scans the pixel matrix to produce a frame is commonly known as, and referenced herein as the "frame rate." The image sensor operates at a predetermined rate.

The camera control unit then compiles each image frame processed using electromagnetic radiation in the visible spectrum to generate a white light video image. Each image frame processed using electromagnetic radiation in the infrared spectrum is also compiled to generate a fluoroscopic video image.

By properly timing the switching of light sources so that the image is illuminated with electromagnetic radiation in the visible spectrum when a white light image frame is exposing, and with electromagnetic radiation in the infrared spectrum when a fluorescent light image frame is exposing, white light and infrared images can be captured in sequential or alternate frames. Inconsistent or mistimed switching may result in insufficient light, incorrect light, or an undesired mixing of light during the exposure of either the white light image frame or the fluorescent light image frame.

Environmental factors such as heat, may affect the operation of the light source, which may cause a phase shift in the timing of the light source switching. For instance, the light source may be turned on after the image sensor begins a new scan of the pixel matrix and only the third or fourth rows are able to collect electromagnetic radiation for image processing. As such, the images may not be fully exposed or uniformly exposed with the correct spectrum of light within a corresponding frame. Such frames may be discarded from video compilation that may lead to an imperfection in the video image.

However, synchronization of the light source with the operation of the image sensor is not needed in all cases. For instance, the imaging system may begin with the image sensor and the light source synchronized with each other. After a period of time, the phase of the light source may be delayed due to timing drift, or changes in circuit delays as a result of temperature.

The actuation of the synchronization unit may increase the processing demands of the imaging system. The imaging system performs other computing functions that also increase processing demands and as such, the processing demands may overload the computing capabilities of the imaging system. For instance, the imaging system performs image processing, data recording and storing, data processing and the like which may affect the performance of the imaging system.

Accordingly, it remains desirable to have an imaging system wherein the synchronization between the light source and the image sensor is adjustable so as to reduce processing demand required to synchronize the light source and the image sensor.

SUMMARY

An imaging system configured to provide a video image is provided. The imaging system includes a camera unit having an image sensor and a light detector unit. The image sensor includes a plurality of pixels that provide image data that is processed to form an image frame. Each image frame includes blank regions of pixels so as to define a blanking region.

A light source is configured to provide electromagnetic radiation the visible spectrum (white light—also referenced herein as "WL") and near infrared spectrum (colored light—also referenced herein as "CL"). Thus, the light source is operable to switch between WL and CL. A camera controller unit processes the time at which electromagnetic radiation, detected by the light detector unit, with the time at which the image sensor is actuated so as to calculate a difference in the actuation of the light source and the image sensor. The difference is compared with the blanking region to determine with the switch is made within a predetermined period.

The system further includes a synchronization unit. The camera controller unit is configured to actuate the synchronization unit so as to adjust the operation of the light source with the operation of the image sensor when the switch is made outside of the predetermined period.

In one aspect, the camera controller unit is configured to process the difference, determine a processing demand of the imaging system and actuate the synchronization unit when the processing demand is below a predetermined threshold and the light source and the image sensor are out of synch with each other. In one aspect, the camera controller unit is configured to process the difference and actuate the synchronization unit when the switch is made outside of the predetermined period.

In one embodiment, the system includes at least two light sources wherein one light source is configured to provide transmit WL and another light source is configured to transmit CL. The light detector is configured to detect electromagnetic radiation from both the range of wavelengths and the time the electromagnetic radiation was emitted.

In one embodiment, the light detector is configured to detect light from the first light source and the second light source, wherein a camera controller unit calculates a difference in time between the actuation of the first light source and the second light source and synchronizes the actuation of the first light source and the second light source when the switch is made outside of the predetermined period.

In one aspect, the camera controller unit is configured to process the differences of the first and second light sources with respect to the image sensor, determine a processing demand of the imaging system and actuate the synchronization unit when the processing demand is below a predetermined threshold even when the switch is made within the predetermined period.

DETAILED DESCRIPTION

Figure 1:
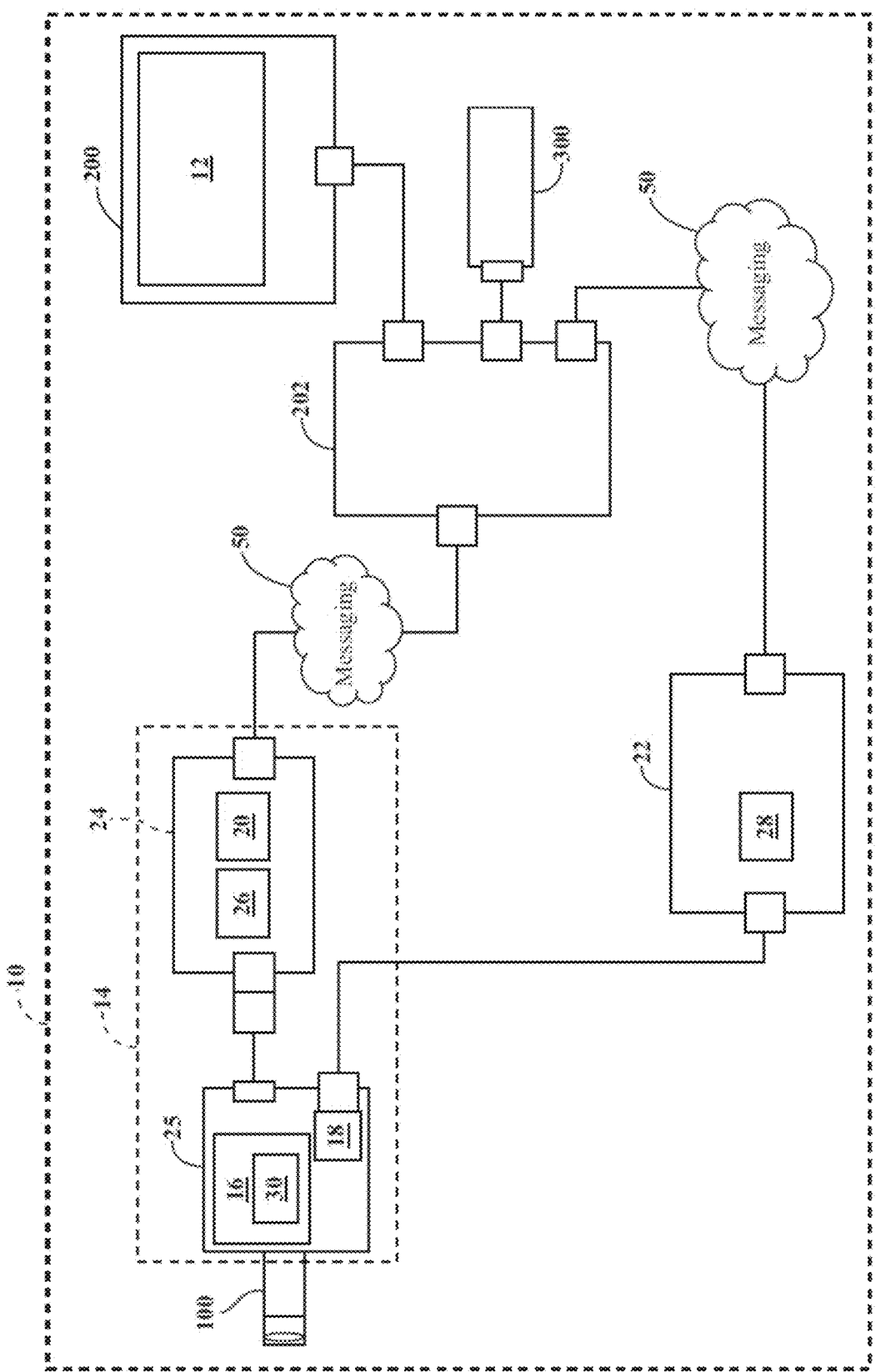
FIG. 1 is a schematic view of a first embodiment of an imaging system according to the principles of the present disclosure.

Referring now to FIG. 1, an imaging system 10 configured to generate a video image 12 is provided. The imaging system 10 includes a camera unit 14 having an image sensor 16 and a light detector unit 18. The imaging system 10 further includes a synchronization unit 20. The imaging system 10 further includes a light source 22 configured to generate one or more types of illumination for irradiating a surgical site. In one aspect, the light source 22 is configured to generate both WL and CL. This may be done by the use of a single light source 22 configured to generate the first and second illumination type, or two light sources 22. The image sensor 16 may be configured to receive reflected or emitted light from the surgical site depending on the type of illumination. The light detector unit 18 detects a change in illumination from the WL to the CL for use in determining the actual time the light source 22 switches. The light detector unit 18 may transmit the actual time of the switch to a camera controller unit 24. The synchronization unit 20 may be part of the light source 22 or the camera controller unit 24.

The camera controller unit 24 processes the actual time light is detected with a timing of the image sensor 16 to detect a difference between the actual time the light source 22 is actuated and the timing of the image sensor 16. The camera controller unit 24 is configured to communicate the difference to the light source 22 so as to synchronize the light source 22 with the image sensor 16 when the difference between the actual time the light source is actuated and the timing of the image sensor 16 is beyond a predetermined period or a processing demand of the imaging system 10 is below a predetermined threshold. As such, processing demand is reduced relative to systems which automatically synchronize the light source 22 with the image sensor 16 when the light source 22 and the image sensor 16 are out of synch with each other.

The image sensor 16 may be configured to actuate at a frequency of 50 or 60 frames per second ("fps") and the light source 22 may also be actuated at the same or similar frequency as the image sensor 16. The frequencies may even be slightly different due to these factors. Despite operating at a same or a similar frequency, the image sensor 16 and light source 22 may be out of phase or become out of phase due to operating on independent internal clocks, which may be affected by heat, component aging, manufacturing tolerances, and other factors. The imaging system 10 further includes an image processor 26 configured to process image data collected by the image sensor 16 so as to generate an image frame. The image sensor 16 operates by exposing the pixels, thus obtaining image data relevant to WL or CL as the case may be. During frame formation, certain pixels will be blank during the same period of time, forming blanking regions. The blanking regions allow for image data to be cleared from the exposed pixels and the image frame to be generated by the active pixels, e.g. pixels exposed and designated for image processing. The light source 22 is configured to switch between WL and CL during the period of blanking region during image frame formation. However, due to phase shifting and slight differences in clock frequencies, the timing of the switch may drift causing disruption to the video quality.

For illustrative purposes, a description of the imaging system 10 is provided within the context of an endoscope system. However, it should be appreciated that the imaging system 10 may be utilized in other applications, illustratively including exoscopes, borescopes, and other imaging systems having two or more illumination types and one or more image sensors. With reference now to FIG. 1, the camera unit 14 is coupled to an endoscope 100 by optics including a plurality of lenses. The camera head 25 is in communication with a camera controller unit 24 through either a cable or a wireless connection. In other examples, the endoscope 100 and camera head 25 may form an integral unit as is known in the art to form a videoscope. In other examples, the camera head 25 and camera controller unit 24 may form an integral unit. Regardless of the specific configuration, the principles of the present disclosure apply to various examples of video imaging systems as previously noted.

As shown in FIG. 1, the endoscope 100 is coupled with a camera head 25 of the camera unit 14. The camera controller unit 24 controls various processing functions of the camera unit 14. The camera controller unit 24 may provide a timing signal to the camera head 25. Alternately, the camera head 25 may generate a timing signal independently of the camera controller unit 24. The camera controller unit 24 and the light source 22 unit operate independently of each other. The light source 22 may include a light outlet for the illumination light near the working end of the endoscope 100 which may be in communication with the light source 22. The light source 22 may be formed by one or more Light Emitting Diodes (LED) within an external light source housing providing "cold light" transmitted via optical fiber connection to the endoscope 100 as known in the art. The light source 22 may be configured to generate electromagnetic radiation in the visible spectrum (commonly called "white light" or "WL") and/or outside the visible spectrum such as NIR and the like for fluorescent imaging applications including ICG (commonly called "color light" or "CL." The light source 22 includes a first timer 28 configured to control the operation of the light source 22. In one example, the first timer 28 is a general purpose timer (GPT) such as a quartz oscillator signal fed through a free running programmable frequency scalers configured to generate a signal of the same rate as the video frame rate (16.67 ms at 60 fps) which is fed though a clocked delay circuit to allow selection of phase shifted version of the frame rate; however it should be appreciated that the first timer may be any other timer currently known or later developed, illustratively including quartz oscillator fed through an FPGA that contains Phase Lock Loops or Delay Lock Loops that can be programmed or configured to implement any desire scaling, frequency multiplication, frequency division, and phase adjustment. Reference to the operation of the light source 22 is described herein as a light phase which includes the period of time in which the light source 22 is actuated and the period of time the light source 22 is turned off.

The image sensor 16 may be on a printed circuit board. The image sensor 16 may be formed in a solid state and include electric components configured to actuate the image sensor 16 for exposure to light as well as clearing the image sensor 16 of any charge from collected light. The electrical components may also include a digital timing control circuit 30, an amplifier (not shown), a filter (not shown), an analog-to-digital converter and the like. The digital timing control circuit 30 controls how long the image sensor 16 is exposed. Reference to the operation of the image sensor 16 is described herein as an exposure phase which includes the time period the image sensor 16 is exposed as well as the time period in which the image sensor 16 is cleared of information.

The image sensor 16 is configured to provide an image of the body cavity to the operator of the endoscope 100, thereby allowing the endoscope 100 operator to locate the treatment area and monitor the medical procedure. The image sensor 16 is in communication with the camera controller unit 24 so as to provide a digital display of the treatment area to a display device 200. The image sensor 16 can be a complementary metal-oxide-semiconductor (CMOS) or a charge-coupled-device (CCD). It should be appreciated that any pixilated image sensor currently known or later developed may be modified and adapted for use herein. In one embodiment, the image sensor 16 is configured to receive electromagnetic radiation in the visible range (e.g., between about 400 nm and 800 nm) and/or near infrared range (e.g., between about 800 nm and 1200 nm) associated with a particular field of view (e.g., area of treatment). As described in greater detail below, the image sensor 16 delivers sensor data to the camera controller unit 24, which processes the sensor data and outputs the data to the display control unit 202 for further formatting into video to one or more display devices 200. The display device 200 may include a display control unit 202 configured to control the visual contents of the display device 200 and the camera controller unit 24 may be integral. The camera controller unit 24 and camera head 25 may be integral.

The image sensor 16 and the light source 22 are configured to cooperate with each other wherein electromagnetic radiation emitted by the light source 22 either is reflected back from tissue or absorbed in tissue and reemitted back so that it is collected by the image sensor 16 and processed into an image frame. However, as stated above, the timing of the image sensor 16 and the light source 22 are independent of each other. In particular, the image sensor 16 is formed of an array of pixels having a plurality of rows and columns. For example, the image sensor may be configured to have 1,280 rows and 1,024 columns, 1920 rows and 1080 columns, or more as sensors continue to increase in resolution up to 4K and 8K resolution at the time of this filing. Frame timing features, commonly associated with rows and columns of an image sensor, are shown with respect to image sensor 16 in FIG. 2.

The light detector unit 18 is positioned so as to detect the presence of electromagnetic radiation transmitted from the light source 22. The light detector unit 18 may be integrated into the image sensor 16 or an independent electrical component mounted to a printed circuit board as generally depicted in FIG. 1. Any light detector unit 18 configured to detect light in the visible spectrum or colored spectrum may be adaptable for use herein, illustratively including a photodiode. The light detector unit 18 may be configured to detect light in the visual spectrum, or colored light such as infrared light. The light detector unit 18 is in communication with the camera controller unit 24. The light detector unit 18 may be, for example, located near the light inlet of the endoscope 100 where electromagnetic radiation first enters the endoscope 100, or alongside the image sensor 16 where it is exposed to the light at the image sensor either directly or from reflection.

The camera controller unit 24 includes non-transitory memory which the image processor 26 can write onto to generate image frames. In some examples, the camera controller unit 24 is configured as a local device integrated in the exoscope or may be a stand-alone computing machine hard wired or wirelessly connected to the exoscope. However, in some examples, the camera controller unit 24 could be configured to operate on a server having data processing hardware and memory hardware.

The non-transitory memory of the camera controller unit 24 may include physical devices used to store programs (e.g., sequences of instructions) or data (e.g., program state information, image data) on a temporary or permanent basis for use by a computing device. The non-transitory memory may be volatile and/or non-volatile addressable semiconductor memory. Examples of non-volatile memory include, but are not limited to, flash memory and read-only memory (ROM), programmable read-only memory (PROM), erasable programmable read-only memory (EPROM), and electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes. It should also be appreciated that further image processing may occur within the camera controller unit 24, or in subsequent unit(s) to process the image for presentation to the user. For example, the display control unit 202 may add a control menu overlay to the displayed image, and may be in the communication path between the camera control unit 24 and the light source 22.

The synchronization unit 20 may be formed of electrical components configured to actuate the light source 22 and adjust the duration, start, and stop times of the light source 22 so as to synchronize the operation of the light source 22 with the operation of the image sensor 16. In one aspect, the camera controller unit 24 actuates the synchronization unit 20 when a switch is made between WL and CL that occurs outside of a predetermined period during a blanking region 999 of image frame generation which is discussed in further detail below.

In another aspect of the imaging system 10, the camera controller unit 24 actuates the synchronization unit 20 when a processing demand of the imaging system 10 is below a predetermined threshold. In such an embodiment, the camera controller unit 24 is configured to determine the processing demand of the imaging system 10. For instance, the camera controller unit 24 may read a read only memory unit of the imaging system 10 to determine the data processing demands, wherein the camera controller unit 24 actuates the synchronization unit 20 so as to synchronize the light source 22 with the image sensor 16 when the processing demand is below a predetermined threshold, even when the switch occurs within the predetermined period. As such, the imaging system 10 is configured to prioritize the synchronization of the light source 22 with the image sensor 16 based upon the processing demand of the imaging system 10, such as image processing functions, data storage, data recording and the like.

The imaging system 10 may communicate using messaging between the camera unit 14, light source 22, and the display control unit 202. For example, message packets 50 transmitted by wired or wireless connections may include error messages generated by the camera unit 14 based on when the switch from WL to CL occurs relative to the predetermined period and predetermined threshold(s). The predetermined period for switching may include zones based on one or more predetermined thresholds. Circuitry and software in the camera unit 14 detect the WL to CL transition, and its relative timing error to the desired "ideal" CL transition. The software would react to the relative timing with respect to timing zones.

For example, there may be timing windows or zones. WL to CL transition in a first timing window, for example, an ideal zone, will not create any error messages. This ideal zone may allow for some timing error. WL to CL transition outside the first timing window, for example, in an early zone, will cause a "small error" message to be sent to the light-source 22, but disruption of the image does not occur. This early zone may allow for an amount of early switch timing error based on a first predetermined threshold. WL to CL transition outside the first timing window, for example, in a late zone, will also cause a "small error" message to be sent to the light-source 22, but disruption of the image does not occur. This late zone may allow for an amount of late switch timing error based on a second predetermined threshold. The second predetermined threshold may have the same absolute value as the first predetermined threshold. WL to CL transition outside a third timing window, for example, in an out of window zone, will cause a "large error" message to be sent, and disruption of image occurs. This out of window zone may require immediate synchronization.

When a CL transition occurs outside of the ideal timing window, the camera unit 14 sends a message to the light source 22 informing it of the transition error. For WL to CL transitions that occur in the early zone or the late zone, immediate synchronization may be desirable but not required. Synchronization may be commanded if processing demand is low enough. However, synchronization may be delayed until the timing error increases. Upon receiving a light transition error message the light source 22 corrects its frame reference timing, and WL-CL transition, by the desired "error" amount. Upon correction of the timing, the light source 22 sends back a message indicating that the desired correction has been performed. The camera unit 14 will wait for the correction performed acknowledgment message from the light source 22, or a message expiration time-out, before sending additional correction requests messages. The message expiration value needs to be larger than the worst case message delay expected for system of devices. The message expiration value may be necessary to recover for a system of devices where the message delivery is not guaranteed, i.e. as in systems that employ wireless communication between devices.

Figure 2:
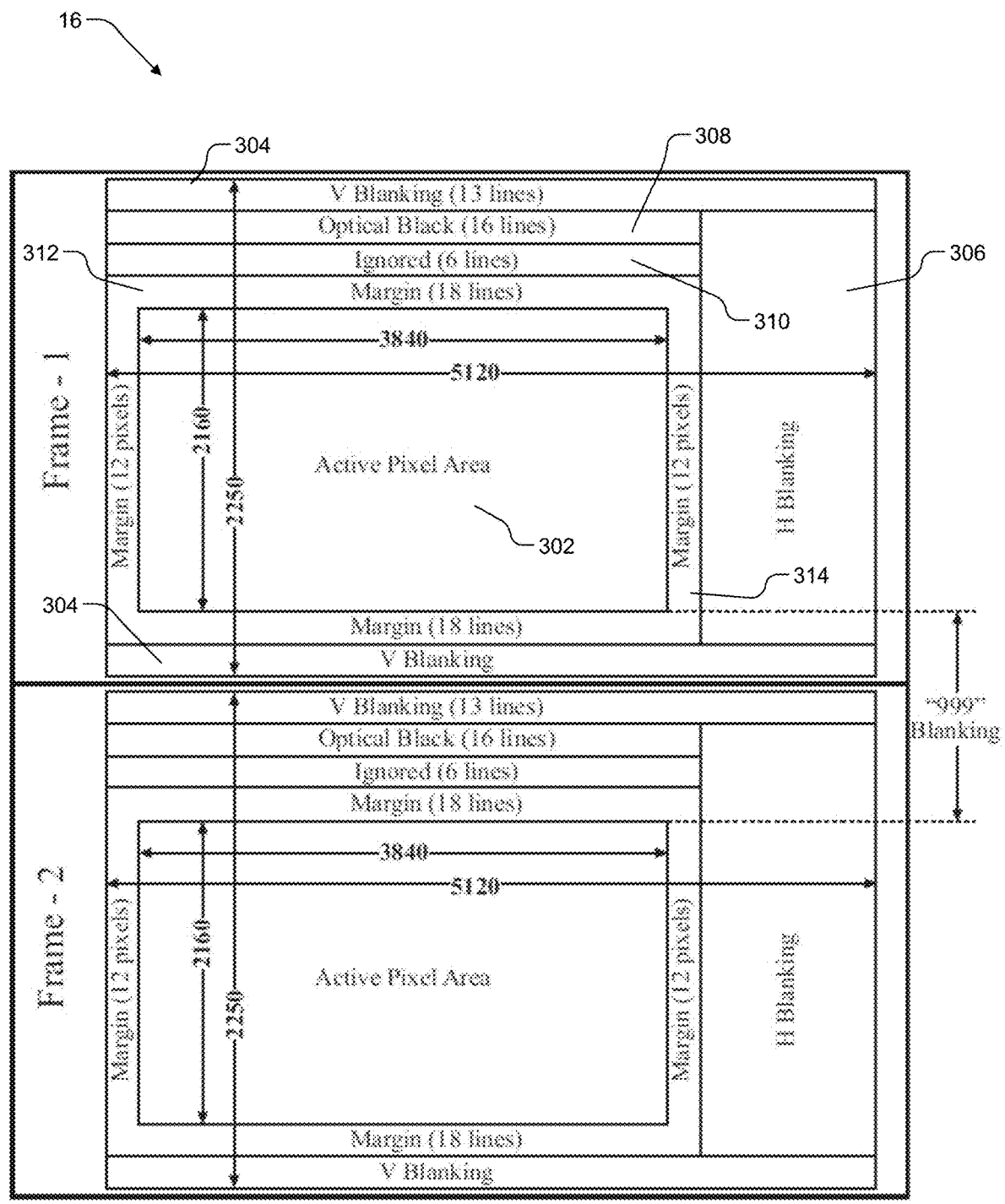
FIG. 2 is a diagram showing the operation of an image sensor according to the principles of the present disclosure.

Operation of the imaging system 10 is further described with reference to FIGS. 2-7. With reference now to FIG. 2, the image sensor 16 output is a line of pixels along with various other data associated with frame formation, timing, and the video signal. The image sensor 16 may be a 4 k sensor with 3840 columns×2160 rows of pixels in an active pixel area 302 and additional lines and columns as known in the art. For example, the start and end of each frame typically includes a number of vertical blanking lines (V Blanking) 304 that correspond to the time between the end of the final line of a frame (such as "Frame-1") and the beginning of the first line of the next frame (such as "Frame-2"). The amount of rows that are associated with V Blanking may be adjusted as known in the art by disabling or otherwise disregarding some of the lines of the active pixel area. For example, image sensor 16 may include thirteen V Blanking lines 304 at the top of a frame and an additional number, such as for example, eighteen V Blanking lines 304 at the bottom of the frame. Horizontal blanking (H Blanking) 306 is another time delay of image processing that occurs at the end of each row. A video signal from an image sensor includes both vertical and horizontal blanking intervals. The vertical blanking occurs between two consecutive frames, while the horizontal blanking interval occurs between two lines. During the blanking period, the video signal is "blanked" by bringing down the voltage to a level equal to or below a black level. "Optical black" lines 308 may be included as reference points for determining black levels. "Ignored" lines 310 may be dummy lines for buffering contamination of adjacent pixels. "Margin" lines 312 or "margin" pixels 314 may be used to delineate the first rows of active pixels for frame formation. Together, these various "inactive periods" of image sensor activity may correspond to the blanking region 999.

Figure 3A:
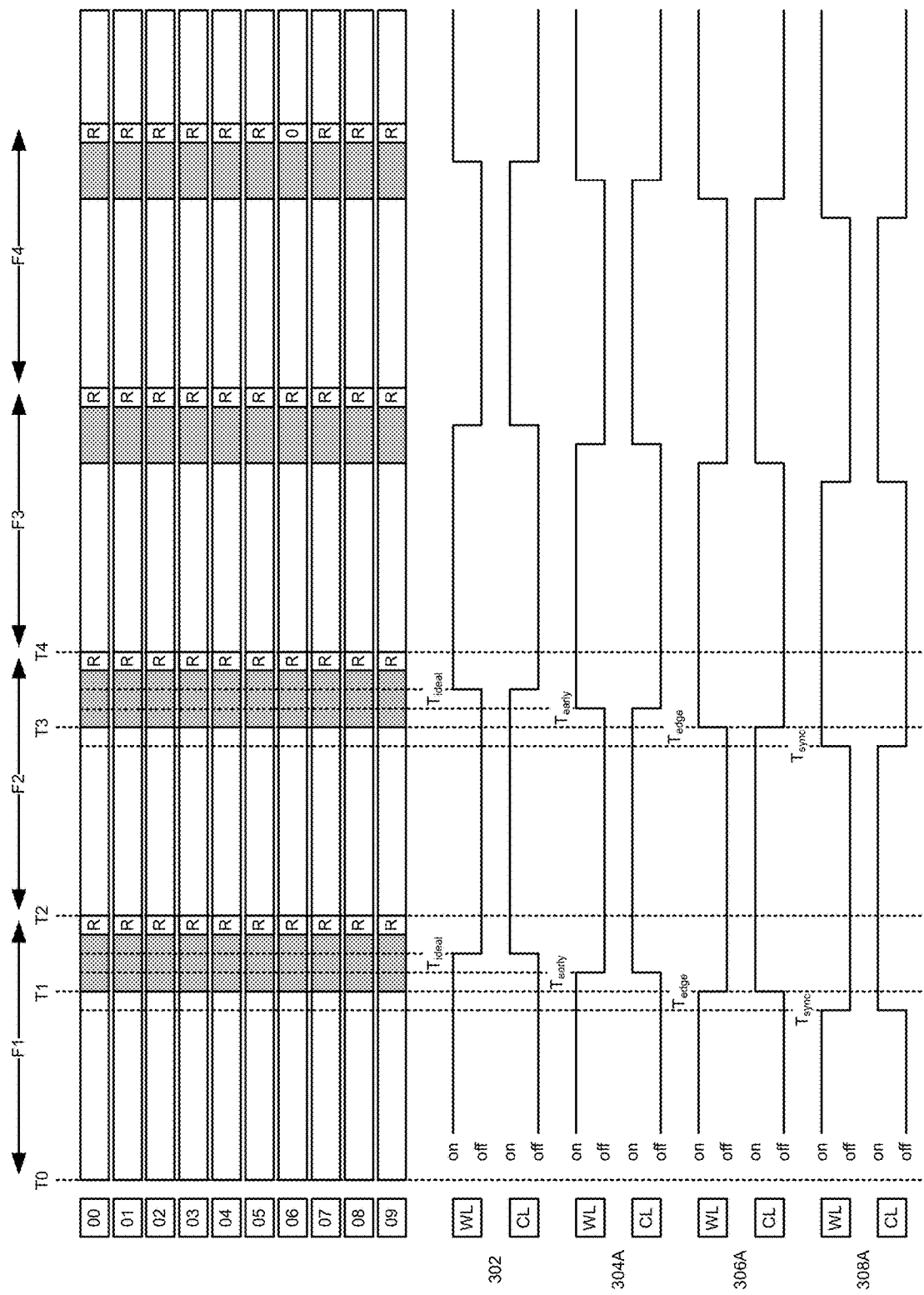
FIGS. 3A and 3B are timing diagrams showing the operation of an image sensor operating using a global shutter mode according to the principles of the present disclosure.
Figure 3B:
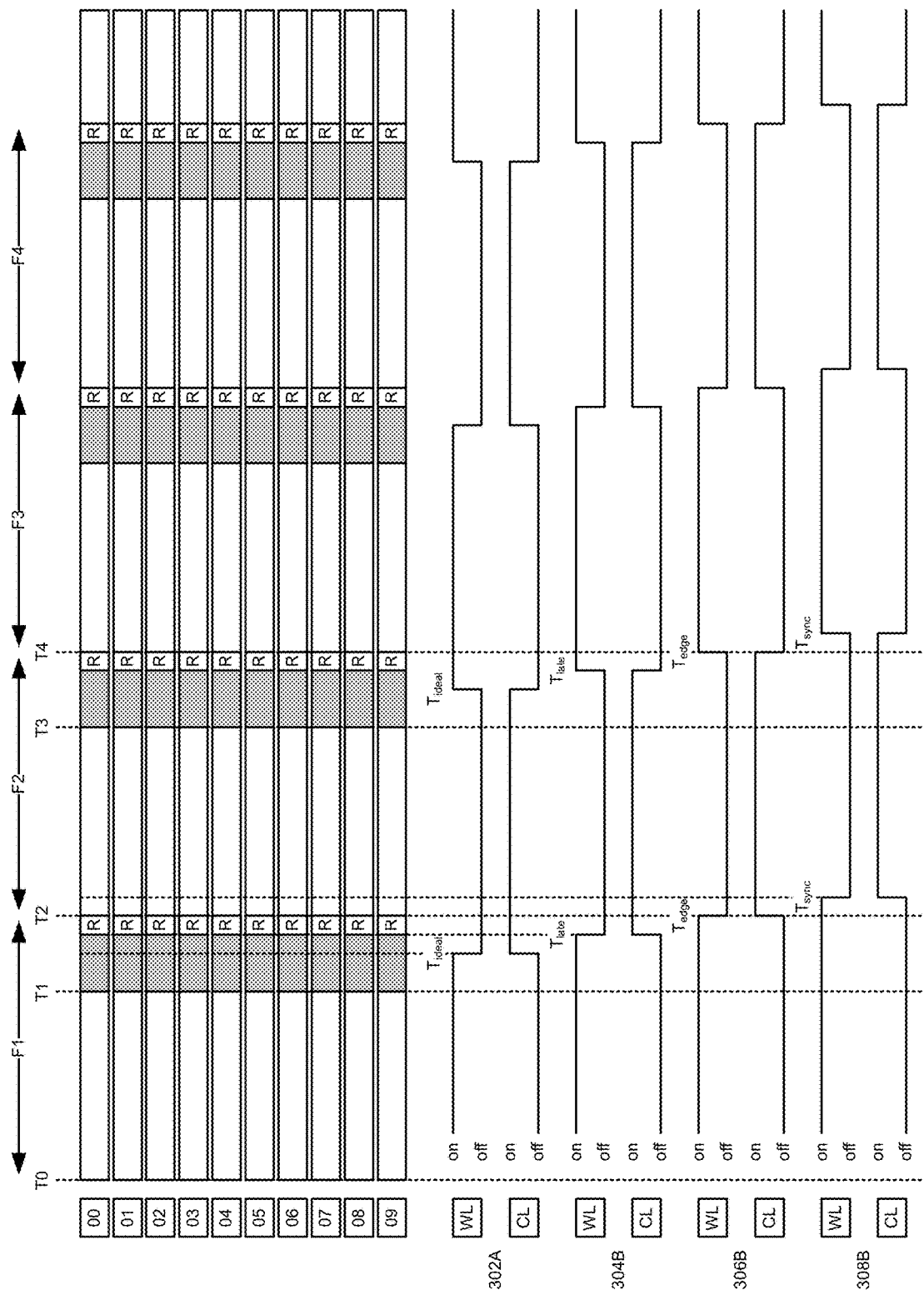
Figure 4A:
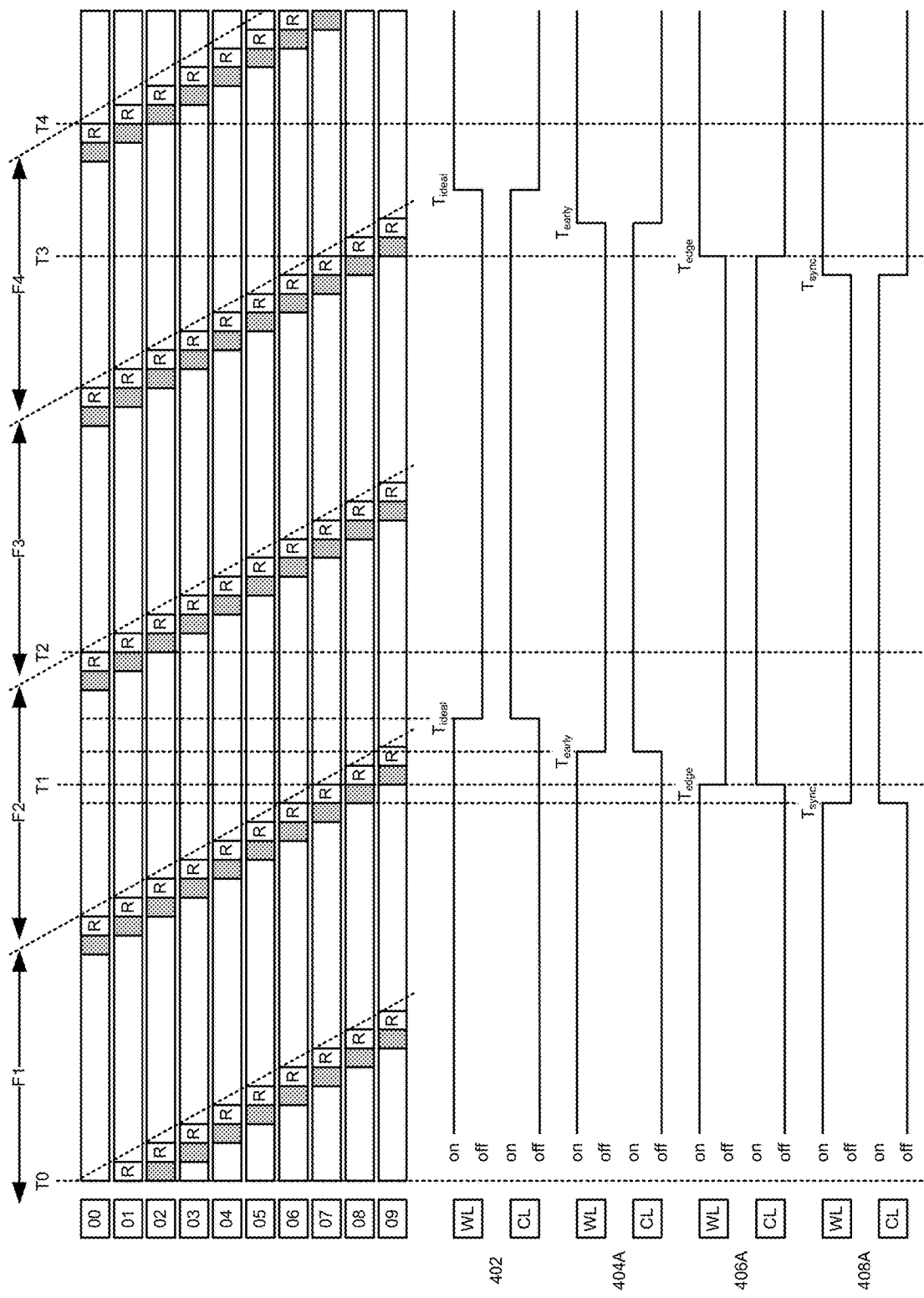
FIGS. 4A and 4B are timing diagrams showing the operation of an image operating using a first rolling shutter mode at full resolution and an effectively reduced frame rate according to the principles of the present disclosure.
Figure 4B:
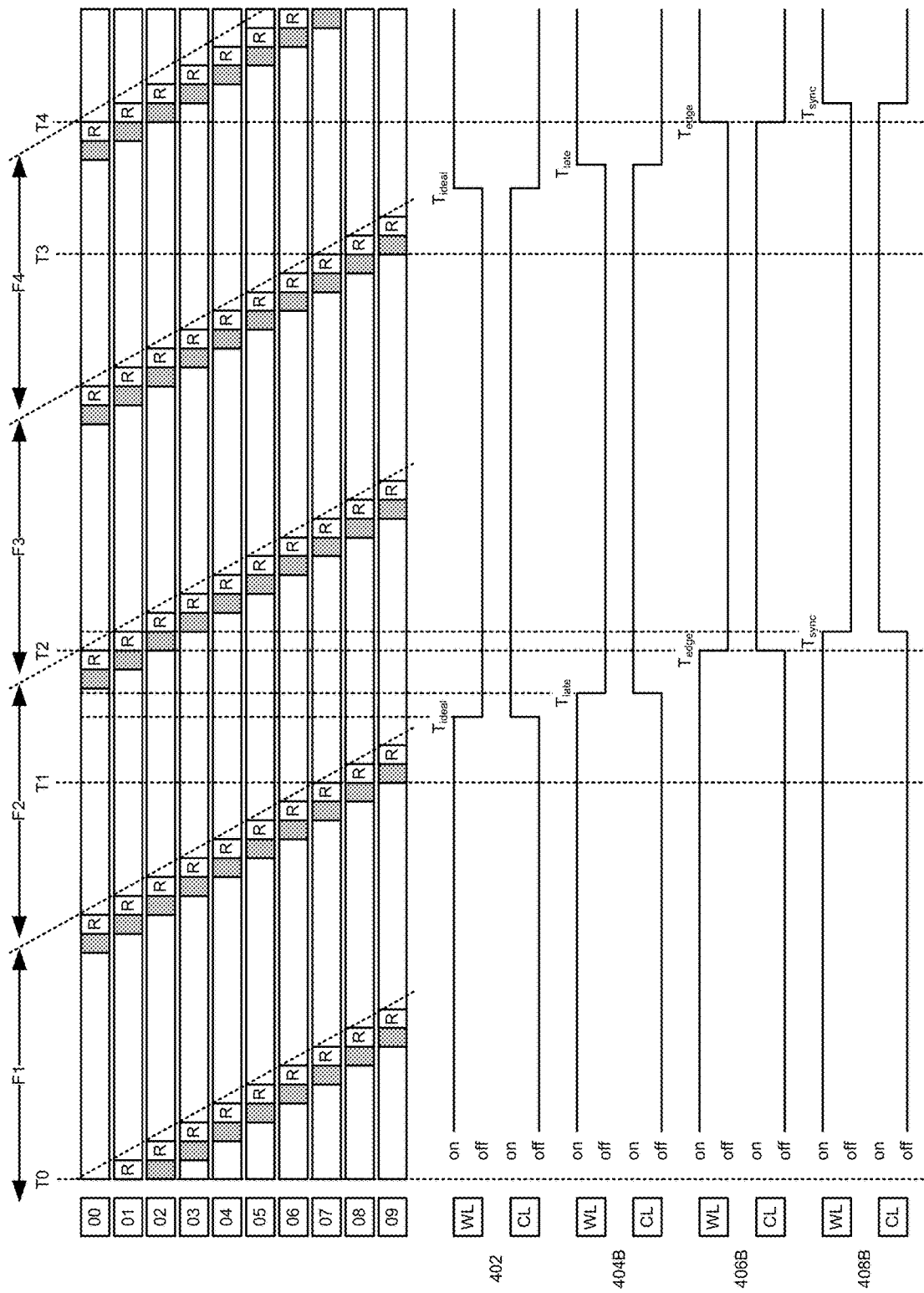
Figure 5A:
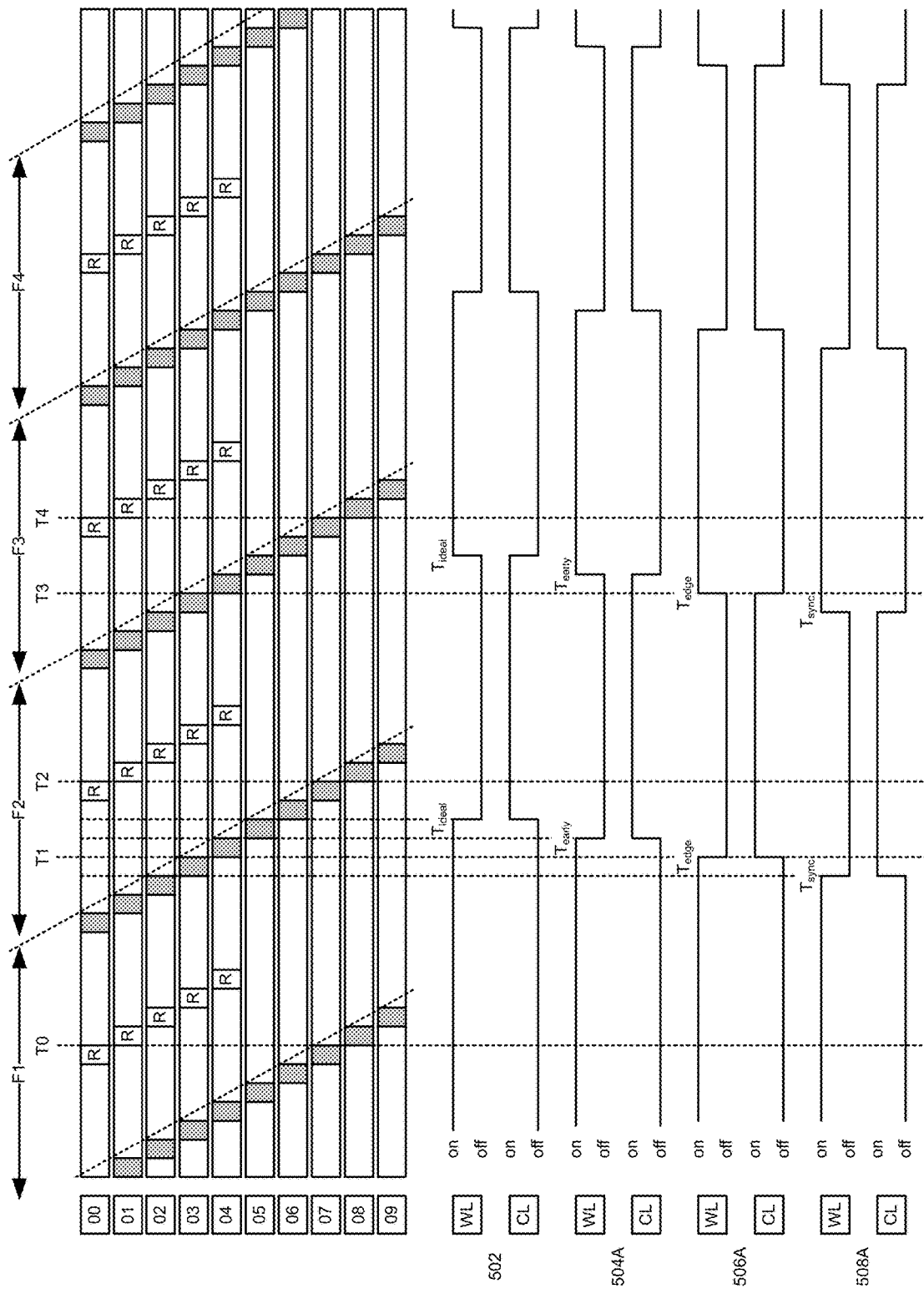
FIGS. 5A and 5B are timing diagrams showing the operation of an image sensor operating using a second rolling shutter mode at reduced resolution and at a full frame rate with reduced exposure time according to the principles of the present disclosure.
Figure 5B:
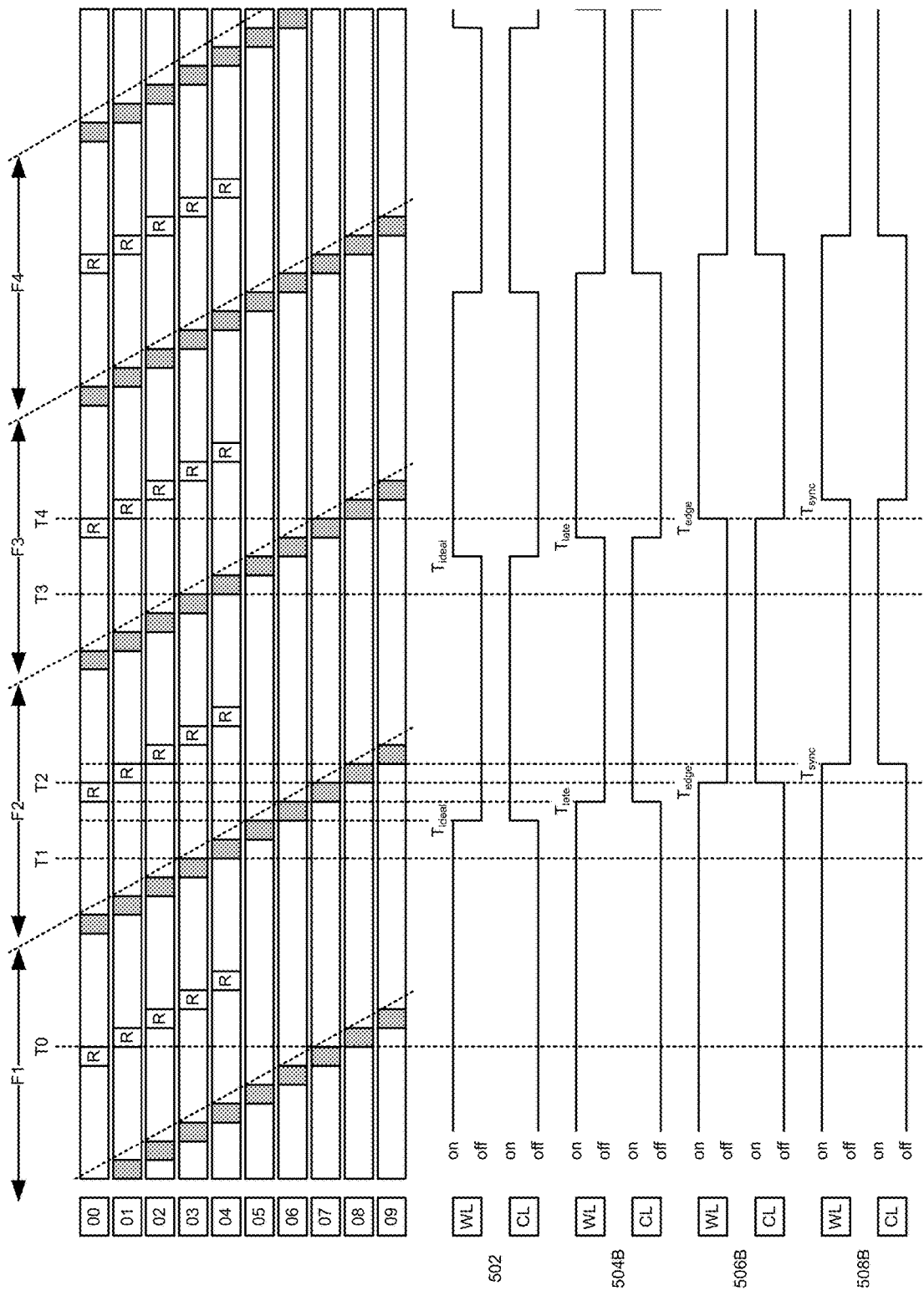

FIGS. 3A-5B illustrate timing sequences for switching between white light (WL) and color light (CL) for different operating modes of the image sensor 16. FIGS. 3A and 3B illustrate a global shutter mode; FIGS. 4A and 4B illustrate a first rolling shutter mode with discarded frames; and FIGS. 5A and 5B illustrate a second rolling shutter mode with exposure control and discarded rows. For illustrative purposes only, image sensor output is shown using only ten rows of pixels, rows 00-09, from an active pixel area of the image sensor. Some additional rows may be binned according to known methods or part of the blanking region 999 of the sensor output. Frames F1-F4 are formed by rows 00-09 over different periods of time indicated by times T0 through T4. Blocks labeled "R" indicate when a reset of a row occurs, for example, when the beginning of the line occurs.

In each of the figures, light source 22 provides both WL and CL at different times relative to the timing of image sensor 16. The timing of the switching on and off of each of the WL and CL are indicated using signal lines that are "on" or "off" for four different light timing sequences. T(ideal) indicates an ideal time for a light to turn on or off with the least chance of disruption of image data. T(early) or T(late) indicates an early or late time respectively for a light to turn on or off but with no disruption of image data. T(edge) indicates an absolute cutoff time for a light to turn on or off else disruption of image data occurs. T(sync) indicates an overly early or overly late time for a light to turn on or off and which would require immediate synchronization.

Global Shutter Mode

Referring now to FIGS. 3A and 3B, the image system 10 is configured to operate the image sensor 16 in a "global shutter mode." In the global shutter mode, video frames F1-F4 are formed from the exposure of pixels in each row 00-09. Each row begins exposing at the same time T0 and ends exposing at the same time T1. Between times T1 and T2, pixel data may be read out and processed into digital form by an A/D converter (shaded regions of rows) and reset (R) in preparation for exposure of the rows 00-09 again. A first frame F1 may be formed from the pixel data of rows 00-09 from time T0 to T2. In a similar fashion as with respect to the first frame F1, each row begins exposing at the same time T2 and ends exposing at the same time T3. Between times T3 and T4, pixel data may be read out and processed into digital form by an A/D converter (shaded region of rows) and reset (R) in preparation for exposure of the rows again, and so on. A second frame F2 may be formed from the pixel data of rows 00-09 from time T2 to T4. Frames F3 and F4 follow the same pattern.

The image sensor timing diagrams further illustrate how the global shutter mode timing of the image sensor may be in synchronization with or may be out of synchronization with the timing of the switch between white light (WL) and color light (CL). As shown in FIGS. 3A and 3B, the light source 22 may simultaneously switch the WL off and the CL on at a first time and subsequently, simultaneously switch the WL on and the CL off at a second time after than the first time. This switching on/off may occur at a light timing frequency corresponding to the frequency of the image sensor frame formation. However, the switching on/off of the WL and CL may be out-of-sync with the image sensor timing as shown in light timing sequences 302-308.

Referring now to FIG. 3A, an ideal light timing 302 illustrates an ideal time T(ideal) for the light source 22 to switch between WL and CL. T(ideal) may be, for example, approximately halfway between T1 and T2, that is T1+(T2−T1)/2. When the detection of a switch between WL and CL occurs at T(ideal), no synchronization is required and therefore, no synchronization or error message is sent. T(ideal) may be centered within an ideal window between T(early) and T(late). A switching of the light source from WL to CL or vice versa during the ideal window of time will result in no disruption of the image frame and no error message 50 being sent to the light source 22. The ideal window of time may be a time during which the pixel data from rows 00-09 are read out and reset and blanking occurs.

Continuing with FIG. 3A, early light source timing 304A illustrates an early time T(early) for the light source 22 to switch between WL and CL. T(early) may be, for example, greater than T1 and less than T(ideal). T(early) may be centered within an early window between T(ideal) and T(edge). A switching of the light source form WL to CL or vice versa during the early window of time will result in no disruption of the image frame and a small error message 50 being sent to the light source 22. The system 10 may force a correction of the light timing if system resources are below a predetermined threshold. However, none of rows 00-09 will be affected because none of the rows 00-09 are exposing.

Continuing further with FIG. 3A, edge light source timing 306A illustrates an edge time T(edge) for the light source 22 to switch between WL and CL. T(edge) may be, for example, greater than T1 and less than T(early). T(edge) may be equal to T1. When the light source 22 switches at time T(edge) or earlier, image disruption will occur. For example, if the timing of the switch is at T(sync), as shown with sync light source timing 308A, rows 00-09 will receive mixed light including both WL and CL. Therefore, if the light source switch occurs at T(edge) or earlier, a large error message 50 may be sent to the light source 22. The system 10 may force a correction of the light timing, regardless of the system resources.

Referring now to FIG. 3B, the ideal light timing 302 is shown again for reference. Late light source timing 304B illustrates a late time T(late) for the light source 22 to switch between WL and CL. T(late) may be, for example, greater than T(ideal) and less than T2. T(late) may be centered within a late window between T(ideal) and T(edge). A switching of the light source form WL to CL or vice versa during the late window of time will result in no disruption of the image frame and a small error message 50 being sent to the light source 22. The system 10 may force a correction of the light timing if system resources are below a predetermined threshold. However, none of rows 00-09 will be affected because none of the rows 00-09 are exposing.

Continuing further with FIG. 3B, edge light source timing 306B illustrates an edge time T(edge) for the light source 22 to switch between WL and CL. T(edge) may be, for example, greater than T(late) and less than T2. T(edge) may be equal to T2. When the light source 22 switches at time T(edge) or later, image disruption will occur. For example, if the timing of the switch is at T(sync), as shown with sync light source timing 308B, rows 00-09 will receive mixed light including both WL and CL. Therefore, if the light source switch occurs at T(edge) or later, a large error message 50 may be sent to the light source 22. The system 10 may force a correction of the light timing, regardless of the system resources.

Rolling Shutter Mode 1

Referring now to FIGS. 4A and 4B, the image system 10 is configured to operate the image sensor 16 in a first "rolling shutter mode" with a reduced effective frame rate. In the first rolling shutter mode, video frames F1-F4 are formed from the exposure of pixels in each row 00-09. In contrast to the global shutter mode, each row begins exposing at a different time, in sequence, with row 00 starting exposure at time T0 and row 09 ending exposure at time T1. Pixel data may be read out after exposure of each row completes. Likewise, a subsequent reset occurs after each row is read out with row 09 completing readout and reset at time T2. A first frame F1 may be formed from the pixel data of rows 00-09 from time T0 to time T1. However, in this example, it is difficult to time the light source switch without disrupting some lines of image data from the second frame F2. Thus, during a portion of the time within frame F2 and/or during the blanking region of some rows of the first frame F1, the light source 22 may be switched as described below. Second frame F2 may be discarded due to a mixture of WL and CL being used during exposure of at least some of rows 00-09. Frames F3 and F4 follow the same pattern.

The image sensor timing diagrams further illustrate how the first rolling shutter mode timing of the image sensor may be in synchronization with or may be out of synchronization with the timing of the switch between white light (WL) and color light (CL). As shown in FIGS. 4A and 4B, the light source 22 may simultaneously switch the WL off and the CL on at a first time and subsequently, simultaneously switch the WL on and the CL off at a second time after than the first time. This switching on/off may occur at a light timing frequency corresponding to the frequency of the image sensor frame formation. However, the switching on/off of the WL and CL may be out-of-sync with the image sensor timing as shown in light timing sequences 402-408.

Referring now to FIG. 4A, an ideal light timing 402 illustrates an ideal time T(ideal) for the light source 22 to switch between WL and CL. T(ideal) may be, for example, approximately halfway between T1 and T2, that is T1+(T2−T1)/2. When the detection of a switch between WL and CL occurs at T(ideal), no synchronization is required and therefore, no synchronization or error message is sent. T(ideal) may be centered within an ideal window between T(early) and T(late). A switching of the light source from WL to CL or vice versa during the ideal window of time will result in no disruption of the image frame and no error message 50 being sent to the light source 22. Rows 00-09 may be exposing at T(ideal) or during the ideal window and receiving a mix of WL and CL. However, pixel data from frame F2 will be discarded.

Continuing with FIG. 4A, early light source timing 404A illustrates an early time T(early) for the light source 22 to switch between WL and CL. T(early) may be, for example, greater than T1 and less than T(ideal). T(early) may be centered within an early window between T(ideal) and T(edge). A switching of the light source form WL to CL or vice versa during the early window of time will result in no disruption of the image frame and a small error message 50 being sent to the light source 22. The system 10 may force a correction of the light timing if system resources are below a predetermined threshold. None of rows 00-09 in F1 will be exposed to a mix of WL and CL.

Continuing further with FIG. 4A, edge light source timing 406A illustrates an edge time T(edge) for the light source 22 to switch between WL and CL. T(edge) may be, for example, greater than T1 and less than T(early). T(edge) may be equal to T1. When the light source 22 switches at time T(edge) or earlier, image disruption will occur. For example, at T(edge), row 09 may begin to receive a mixture of WL and CL. If the timing of the switch is at T(sync), as shown with sync light source timing 408A, row 09 will receive mixed light including both WL and CL. Therefore, if the light source switch occurs at T(edge) or earlier, a large error message 50 may be sent to the light source 22. The system 10 may force a correction of the light timing, regardless of the system resources.

Referring now to FIG. 4B, the ideal light timing 402 is shown again for reference. Late light source timing 404B illustrates a late time T(late) for the light source 22 to switch between WL and CL. T(late) may be, for example, greater than T(ideal) and less than T2. T(late) may be centered within a late window between T(ideal) and T(edge). A switching of the light source form WL to CL or vice versa during the late window of time will result in no disruption of the image frame and a small error message 50 being sent to the light source 22. The system 10 may force a correction of the light timing if system resources are below a predetermined threshold. None of rows 00-09 in F3 will be exposed to a mix of WL and CL.

Continuing further with FIG. 4B, edge light source timing 406B illustrates an edge time T(edge) for the light source 22 to switch between WL and CL. T(edge) may be, for example, greater than T(late) and less than T2. T(edge) may be equal to T2. When the light source 22 switches at time T(edge) or later, image disruption will occur. For example, at T(edge), row 00 may begin to receive a mixture of WL and CL. If the timing of the switch is at T(sync), as shown with sync light source timing 408B, row 00 will receive mixed light including both WL and CL. Therefore, if the light source switch occurs at T(edge) or later, a large error message 50 may be sent to the light source 22. The system 10 may force a correction of the light timing, regardless of the system resources.

Rolling Shutter Mode 2

Referring now to FIGS. 5A and 5B, the image system 10 is configured to operate the image sensor 16 in a second "rolling shutter mode" with a reduced effective resolution due to additional binning and blanking. In the second rolling shutter mode, video frames F1-F4 are formed from the exposure of pixels in each row 00-09. Similar to the first rolling shutter mode, each row begins exposing at a different time, in sequence, with row 00 starting exposure at time T0 and row 04 ending exposure at time T1. Pixel data may be read out after exposure of each row completes. Rows 05-09 may be combined with rows 00-04 through a vertical binning process. A first frame F1 may be formed from the pixel data of rows 00-09 from time T0 to time T1. However, because of the binning process, the a portion of the frame F1 and frame F2 time associated with exposing rows 05-09 may overlap with the time the light source switches without disrupting the reduced resolution image data. Thus, during a portion of the time within frame F1 and frame F2, the light source 22 may be switched as described below.

The image sensor timing diagrams further illustrate how the second rolling shutter mode timing of the image sensor may be in synchronization with or may be out of synchronization with the timing of the switch between white light (WL) and color light (CL). As shown in FIGS. 5A and 5B, the light source 22 may simultaneously switch the WL off and the CL on at a first time and subsequently, simultaneously switch the WL on and the CL off at a second time after than the first time. This switching on/off may occur at a light timing frequency corresponding to the frequency of the image sensor frame formation. However, the switching on/off of the WL and CL may be out-of-sync with the image sensor timing as shown in light timing sequences 502-508.

Referring now to FIG. 5A, an ideal light timing 502 illustrates an ideal time T(ideal) for the light source 22 to switch between WL and CL. T(ideal) may be, for example, approximately halfway between T1 and T2, that is T1+(T2−T1)/2. When the detection of a switch between WL and CL occurs at T(ideal), no synchronization is required and therefore, no synchronization or error message is sent. T(ideal) may be centered within an ideal window between T(early) and T(late). A switching of the light source from WL to CL or vice versa during the ideal window of time will result in no disruption of the image frame and no error message 50 being sent to the light source 22. Rows 00-04 may be exposing at T(ideal) or during the ideal window and receive a mix of WL and CL. However, pixel data will be reset before exposure of rows 00-04 for formation of frame F2.

Continuing with FIG. 5A, early light source timing 504A illustrates an early time T(early) for the light source 22 to switch between WL and CL. T(early) may be, for example, greater than T1 and less than T(ideal). T(early) may be centered within an early window between T(ideal) and T(edge). A switching of the light source form WL to CL or vice versa during the early window of time will result in no disruption of the image frame and a small error message 50 being sent to the light source 22. The system 10 may force a correction of the light timing if system resources are below a predetermined threshold. None of rows 00-04 in F1 will be exposed to a mix of WL and CL.

Continuing further with FIG. 5A, edge light source timing 506A illustrates an edge time T(edge) for the light source 22 to switch between WL and CL. T(edge) may be, for example, greater than T1 and less than T(early). T(edge) may be equal to T1. When the light source 22 switches at time T(edge) or earlier, image disruption will occur. For example, at T(edge), row 04 may begin to receive a mixture of WL and CL. If the timing of the switch is at T(sync), as shown with sync light source timing 508A, rows 04 will receive mixed light including both WL and CL. Therefore, if the light source switch occurs at T(edge) or earlier, a large error message 50 may be sent to the light source 22. The system 10 may force a correction of the light timing, regardless of the system resources.

Referring now to FIG. 5B, the ideal light timing 502 is shown again for reference. Late light source timing 404B illustrates a late time T(late) for the light source 22 to switch between WL and CL. T(late) may be, for example, greater than T(ideal) and less than T2. T(late) may be centered within a late window between T(ideal) and T(edge). A switching of the light source form WL to CL or vice versa during the late window of time will result in no disruption of the image frame and a small error message 50 being sent to the light source 22. The system 10 may force a correction of the light timing if system resources are below a predetermined threshold. None of rows 00-04 in F2 will be exposed to a mix of WL and CL.

Continuing further with FIG. 5B, edge light source timing 506B illustrates an edge time T(edge) for the light source 22 to switch between WL and CL. T(edge) may be, for example, greater than T(late) and less than T2. T(edge) may be equal to T2. When the light source 22 switches at time T(edge) or later, image disruption will occur. For example, at T(edge), row 00 may begin to receive a mixture of WL and CL. If the timing of the switch is at T(sync), as shown with sync light source timing 508B, rows 00 will receive mixed light including both WL and CL. Therefore, if the light source switch occurs at T(edge) or later, a large error message 50 may be sent to the light source 22. The system 10 may force a correction of the light timing, regardless of the system resources.

Figure 6:
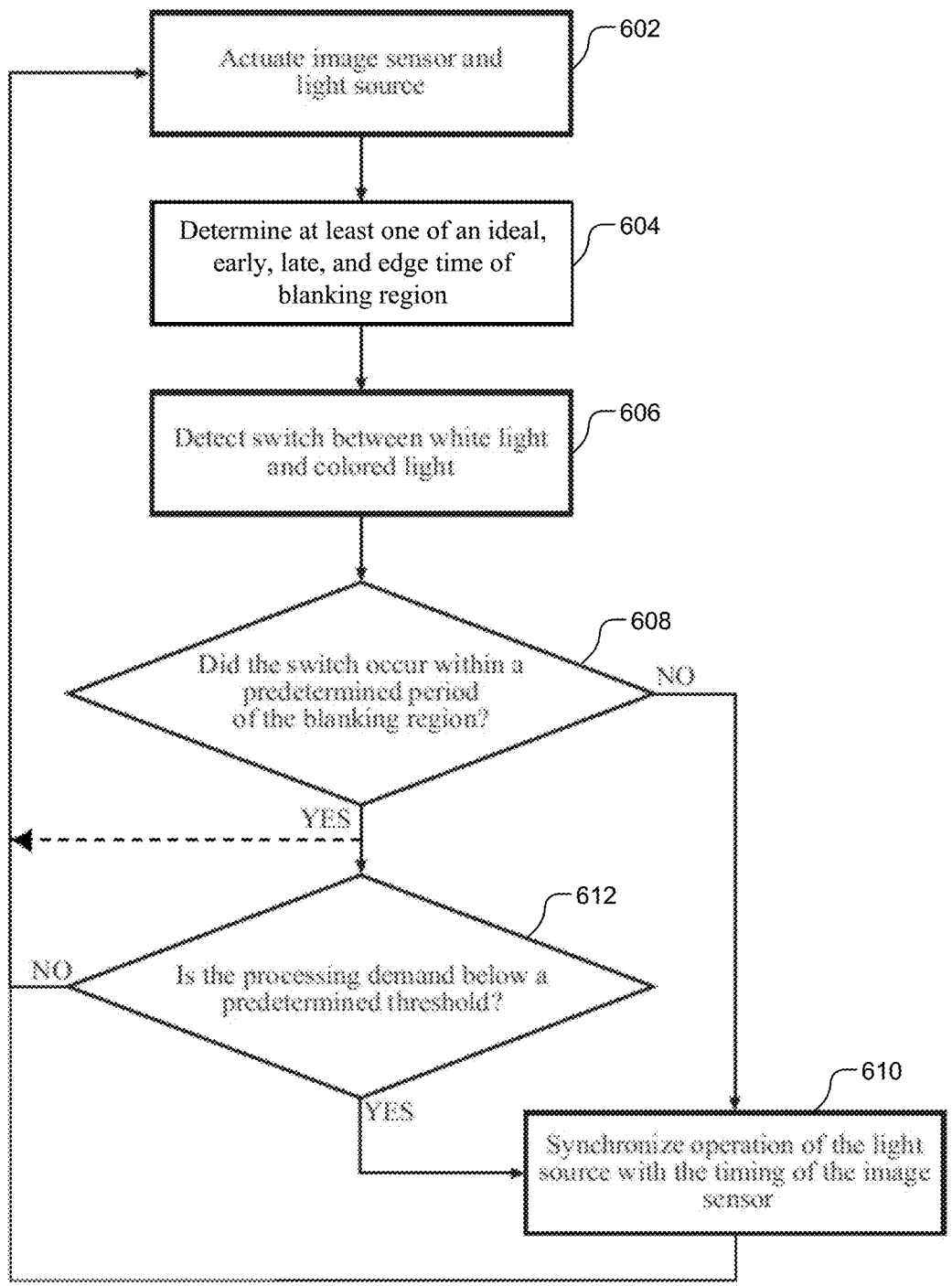
FIG. 6 is a flow chart showing a method of synchronizing a light source with an image sensor according to the principles of the present disclosure.

With reference now to FIG. 6, a method of synchronizing the light source 22 with the image sensor 16 is provided. The method is carried out in an imaging system 10 having a camera unit 14 having an image sensor 16 and a light detector unit 18. The imaging system 10 includes a synchronization unit 20 configured to actuate a light source 22 so as to synchronize the operation of the light source 22 with the operation of the image sensor 16 when the difference between the timing of the light source 22 and the timing of the image sensor 16 is beyond a predetermined threshold. The light source 22 is configured to switch from transmitting WL to transmitting CL.

In step 602, the image sensor 16 and light source 22 begin exposing and illuminating respectively. In step 604, the system 10 determines an ideal time for switching base on the timing of the image sensor 16. The method may include determining an ideal window of time for switching. The method may include determining an early time for switching and a late time for switching. The ideal window may include the period between the early time and the late time. The method may include determining an early window of time for switching and a late window of time for switching as described above. The method may include determining edge times for switching, including an early edge time and a late edge time. The period of time the blanking region occurs may be between the early edge time and the late edge time.

In step 606, the method proceeds to detecting the time a switch is made between WL and CL using, for example the light detector unit 18. In step 608, the method proceeds to determining if the switch is made within the ideal window, the early window, the late window, or outside the edge times. If the switch is made within the ideal window, then the process returns to 602. If the switch is made outside the ideal window, for example in the early window or the late window, the process may return to 602 and send a small error message. If the switch is made outside the early edge time and the late edge time, a large error message is sent and a synchronization of the light source 22 with the image sensor 16 occurs at step 610.

In one aspect of the method, the method may include the step of determining the processing demand of the imaging system 10 at step 612. In such an instance, the method includes the step of determining if the processing demand is above a predetermined threshold, e.g. high. If the processing demand is high and the switch occurs outside the ideal window, for example in the early window or the late window, the synchronization unit 20 is not actuated and the image sensor 16 and the light source 22 continue to operate in their current timing. However, if the processing demand is low, e.g. below the predetermined threshold established for processing demand, the synchronization unit 20 is actuated.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An imaging system configured to generate an image frame comprising:
   a camera unit having an image sensor, a light detector unit, and a camera controller unit;
   a light source configured to switch between transmitting white light and colored light,
      wherein the light detector unit detects an actual time the light source is switched and transmits the actual time to the camera controller unit,
      wherein the camera controller unit processes the actual time to determine if the light source switches between transmitting white light and colored light within a predetermined period of time during a blanking region of a generation of the image frame; and
   a synchronization unit configured to synchronize the switch between transmitting white light and colored light.

2. The imaging system of claim 1, wherein the ideal time includes a window of time during the blanking region.

3. The imaging system of claim 2, wherein the ideal time includes a plurality of predetermined timing windows.

4. The imaging system of claim 3, wherein the synchronization unit does not synchronize the switch message when the error amount is within a first timing window.

5. The imaging system of claim 1, wherein the camera controller unit actuates the synchronization unit when a processing demand of the imaging system is less than a predetermined processing threshold.

6. The imaging system of claim 5, wherein the synchronization unit sends a synchronization message from the camera unit to the light source to synchronize the switch.

7. The imaging system of claim 4, wherein the synchronization unit synchronizes the switch when the error amount is outside the first timing window and the processing demand of the imaging system is less than the predetermined processing threshold.

8. The imaging system of claim 6, wherein the synchronization unit sends a synchronization message when the error amount is outside a second timing window that is wider than the first timing window.

9. The imaging system of claim 1, wherein the image sensor performs a rolling shutter readout.

10. The imaging system of claim 9, wherein the image sensor includes a matrix of active pixels having at least 1920 columns and 1080 rows.

11. The imaging system of claim 1, wherein the light detector unit is disposed in the camera unit.

12. The imaging system of claim 1, wherein the light source comprises a first light source and a second light source.

13. The imaging system of claim 12, wherein the first light source comprises a white light source and the second light source comprises a near infrared light source.

14. A method of synchronizing a light source with an image sensor in an imaging system, the method comprising:
   providing a camera unit having the image sensor and a light detector unit;
   providing a synchronization unit configured to actuate the light source, the light source switching between transmitting white light and colored light;
   determining a blanking region during image frame formation;
   detecting if the switch between transmitting white light and colored light is made within a predetermined period of time of the blanking region; and
   synchronizing the light source with the image sensor based on an error amount.

15. The method as set forth in claim 14, wherein the error amount is based on a switch being made outside of an ideal time for the light source to be switched.

16. The method as set forth in claim 15, further including the step of determining a processing demand of the imaging system.

17. The method as set forth in claim 16, further including the step of synchronizing the light source with the image sensor when the switch occurs within the predetermined period of time and the processing demand of the imaging system is below a predetermined threshold.

* * * * *